United States Patent
Miyamoto et al.

(10) Patent No.: US 6,201,015 B1
(45) Date of Patent: Mar. 13, 2001

(54) THERAPEUTIC METHOD FOR THROMBOCYTOPATHY TREATMENT

(75) Inventors: Mitsuko Miyamoto; Naohiro Yamada; Atsushi Ohtake; Hisanori Wakita, all of Kanagawa (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 09/068,807

(22) PCT Filed: Sep. 17, 1997

(86) PCT No.: PCT/JP97/03287

§ 371 Date: May 27, 1998

§ 102(e) Date: May 27, 1998

(87) PCT Pub. No.: WO98/11899

PCT Pub. Date: Mar. 26, 1998

(30) Foreign Application Priority Data

Sep. 17, 1996 (JP) .................................... 8-245078

(51) Int. Cl.⁷ ................................... A61K 31/34

(52) U.S. Cl. ............................................. 514/468

(58) Field of Search ................... 549/299, 458; 514/468

(56) References Cited

U.S. PATENT DOCUMENTS

| | | | | |
|---|---|---|---|---|
| 4,474,802 | * | 10/1984 | Ohno et al. | 549/458 |
| 4,564,620 | * | 1/1986 | Ohno et al. | 514/337 |
| 5,416,231 | * | 5/1995 | Asai et al. | 549/465 |

* cited by examiner

Primary Examiner—Amelia Owens
(74) Attorney, Agent, or Firm—Austin R. Miller

(57) ABSTRACT

A platelet function increment agent including a prostaglandin $I_2$ derivative as an active ingredient, and a therapeutic method for thrombocytopathy using the same.

The platelet function increment agent of the present invention does not induce platelet aggregation, has superior activating action on platelets and is greatly useful as a platelet function increment agent.

8 Claims, No Drawings

THERAPEUTIC METHOD FOR THROMBOCYTOPATHY TREATMENT

This application is a 371 of PCT/JP97/03287 filed Sep. 17, 1997.

TECHNICAL FIELD

The present invention relates to a platelet function increment agent and a therapeutic method for treating thrombocytopathy with a prostaglandin $I_2$ derivative.

BACKGROUND ART

Diseases which exhibit hemorrhagic diathesis due to platelet function incline even when the platelet count is within a normal range, are generically called thrombocytopathy. Such thrombocytopathy is classified into congenital thrombocytopathy and acquired thrombocytopathy. Congenital thrombocytopathy is further classified into abnormalities in adhesion, aggregation and releasing based upon the species of the abnormalities.

Acquired thrombocytopathy has a higher frequency than that of congenital thrombocytopathy and, for example, occurs with a variety of diseases such as chronic renal failure, liver diseases and blood disorders, or is attributed to extracorporeal circulation or use of drugs. Further, administration of any of the aforementioned drugs to such a disease exhibiting hemorrhagic diathesis enhances hemorrhagic diathesis and hence is dangerous. Therefore, prevention of such diseases, and of hemorrhagic diathesis due to the use of a drug, is required.

To these congenital platelet abnormalities in release and acquired thrombocytopathy, DDAVP (1-diamino 8-D-arginine vasopressin) and other agents are applied, but these drugs may induce arterial thrombosis and/or hyponatremia as adverse drug reactions. In an emergency, platelet transfusion may be conducted, but this treatment may invite a serious adverse reaction or side effect due to production of antibodies to platelets or lymphocytes.

Meanwhile, prostaglandin $I_2$ (PGI$_2$, prostacyclin, referred to in Nature, 1976;268:688) is known as a substance having strong antiplatelet activity and telangiectatic activity. Since this substance has an unstable exo-enol structure, it is extremely unstable even in a neutral aqueous solution and is converted into 6-oxo-PGF$_{1\alpha}$ which has almost no physiological activity (bioactivity). The instability of PGI$_2$ is markedly disadvantageous when this compound is intended to be used as a drug. Further disadvantageously, PGI$_2$ is unstable in vivo and its activity is not long-lasting. As a compound in which these defects are markedly improved, a PGI$_2$ derivative having a skeleton obtained by converting an exo-enol moiety which characterizes PGI$_2$ to an inter-m-phenylene structure, i.e., a 4,8-inter-m-phenylene-prostaglandin $I_2$ derivative is described in the specifications of Japanese Examined Patent Publication No. 6-62599 and the like. This PGI$_2$ derivative has already been known to have antiplatelet activity, vasodilating activity, gastric acid inhibitory activity, bronchial muscle relaxant activity, uterine contraction activity and other activities. Its platelet function increment activity has, however, not been known, and its usefulness as a platelet function increment agent has been first found by us.

In addition, there are chemically stable PGI$_2$ derivatives having modified skeletons obtained by converting the structure to a carbacyclin structure or an isocarbacyclin structure. These PGI$_2$ derivatives, however, have not yet been reported to intensify or enhance platelet function in the presence of a thromboxane $A_2$ agonist (hereinafter referred to as a "TXA$_2$") antagonist, though they have antiplatelet activities. Hence, it has not been known that these derivatives exhibit platelet function increasing or enhancing activity without the intermediation of TXA$_2$ receptors.

It is an object of the present invention to provide a platelet function increment agent which by itself does not induce platelet aggregation but enhances the function of platelets sufficiently, and a therapeutic method for treatment of thrombocytopathy.

SUMMARY OF THE INVENTION

The present invention relates to a platelet function increment agent comprising a prostaglandin $I_2$ derivative as an active ingredient, and to a therapeutic method for thrombocytopathy using the same.

BEST MODE FOR CARRYING OUT THE INVENTION

The prostaglandin $I_2$ derivative used in the present invention includes, but is not limited to, carbacyclin, isocarbacyclin, meta-phenylene-form prostaglandin $I_2$ derivatives and the like. Preferably, a meta-phenylene-form prostaglandin $I_2$ derivative is used, and particularly preferably, a 4,8-inter-m-phenylene-prostaglandin derivative having the following general formula (I) (hereinafter referred to as "the present prostaglandin $I_2$ derivative") or its pharmacologically acceptable salt.

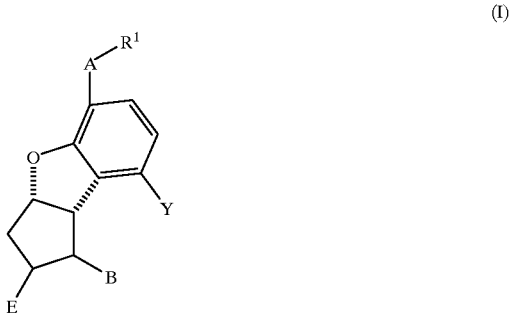

(I)

[wherein $R^1$ is,
(A) COOR$^2$
wherein R$^2$ is,
1) a hydrogen or a pharmacologically acceptable cation,
2) a straight-chain alkyl having 1 to 12 carbon atoms or a branched alkyl having 3 to 14 carbon atoms,
3) —Z—R$^3$
wherein Z is a balance bond, or a straight-chain or branched alkylene shown by C$_t$H$_{2t}$, t represents an integer from 1 to 6, R$^3$ is a cycloalkyl having 3 to 12 carbon atoms or a substituted cycloalkyl having 3 to 12 carbon atoms which is substituted with 1 to 3 substituents R$^4$, where R$^4$ is a hydrogen atom or an alkyl group having 1 to 5 carbon atoms,
4) —(CH$_2$CH$_2$O)$_n$CH$_3$
wherein n is an integer from 1 to 5,
5) —Z—Ar$^1$
wherein Z has the same meaning as defined above, Ar$^1$ is phenyl, α-naphthyl, β-naphthyl, 2-pyridyl, 3-pyridyl, 4-pyridyl, α-furyl, β-furyl, α-thienyl, β-thienyl or a substituted phenyl (wherein the substituent is at least one chlorine, bromine, fluorine, iodine, trifluoromethyl, an alkyl having 1 to 4 carbon atoms, nitro, cyano, methoxy, phenyl, phenoxy, p-acetamidebezamide, —CH=N—NH—C(=O)—NH$_2$, —NH—C(=O)—Ph, —NH—C(=O)—CH$_3$ or —NH—C(=O)—NH$_2$), 6) —C$_t$H$_{2t}$COOR$^4$
   wherein C$_t$H$_{2t}$ and R$^4$ have the same meanings as defined above, 7) —C$_t$H$_{2t}$N(R$^4$)$_2$
   wherein C$_t$H$_{2t}$ and R$^4$ have the same meanings as defined above, 8) —CH(R$^5$)—C(=O)—R$^6$
   wherein R$^5$ is a hydrogen or benzoyl, R$^6$ is phenyl, p-bromophenyl, p-chlorophenyl, p-biphenyl, p-nitrophenyl, p-benzamidephenyl or 2-naphthyl, 9) C$_p$H$_{2p}$—W—R$^7$
   wherein W is —CH=CH—, —CH=CR$^7$— or —C≡C—, R$^7$ is a hydrogen, or a straight-chain or branched alkyl or aralkyl each having 1 to 30 carbon atoms, p is an integer from 1 to 5, or, 10) —CH(CH$_2$OR$^8$)$_2$
    wherein R$^8$ is an alkyl or acyl each having 1 to 30 carbon atoms, (B) —CH$_2$OH (C) —C(=O)N(R$^9$)$_2$
    wherein R$^9$ is a hydrogen, a straight-chain alkyl having 1 to 12 carbon atoms, a branched alkyl having 3 to 12 carbon atoms, a cycloalkyl having 3 to 12 carbon atoms, a cycloalkylalkylene having 4 to 13 carbon atoms, phenyl, a substituted phenyl (wherein the substituent has the same meaning as defined in the above item (A) 5)), an aralkyl having 7 to 12 carbon atoms or —SO$_2$R$^{10}$, where R$^{10}$ is an alkyl having 1 to 10 carbon atoms, a cycloalkyl having 3 to 12 carbon atoms, phenyl, a substituted phenyl (wherein the substituent has the same meaning as defined in the above item (A) 5)) or an aralkyl having 7 to 12 carbon atoms, and two of the substituents R$^9$ may be the same or different provided that when one is —SO$_2$R$^{10}$, the other is not —SO$_2$R$^{10}$, or, (D) —CH$_2$OTHP (where THP is a tetrahydropyranyl group);

A is,

1) —(CH$_2$)$_m$—
2) —CH=CH—CH$_2$—
3) —CH$_2$—CH=CH—
4) —CH$_2$—O—CH$_2$—
5) —CH=CH—
6) —O—CH$_2$— or
7) —C≡C—
   wherein m is an integer of 1 or 2, Y is a hydrogen, an alkyl having 1 to 4 carbon atoms, chlorine, bromine, fluorine, formyl, methoxy or nitro;

B is,

—X—C(R$^{11}$)(R$^{12}$)OR$^{13}$ wherein R$^{11}$ is a hydrogen or an alkyl having 1 to 4 carbon atoms, R$^{13}$ is a hydrogen, an acyl having 1 to 14 carbon atoms, an aroyl having 6 to 15 carbon atoms, tetrahydropyranyl, tetrahydrofuranyl, 1-ethoxyethyl or t-butyl;

X is,
1) —CH$_2$—CH$_2$—
2) —CH=CH—
3) —C≡C—,

R$^{12}$ is, 1) a straight-chain alkyl having 1 to 12 carbon atoms, a branched alkyl having 3 to 14 carbon atoms or, 2) —Z—Ar$^2$
   wherein Z has the same meaning as defined above, Ar$^2$ is phenyl, α-naphthyl, β-naphthyl, or a phenyl substituted with at least one chlorine, bromine, fluorine, iodine, trifluoromethyl, an alkyl having 1 to 4 carbon atoms, nitro, cyano, methoxy, phenyl or phenoxy, or 3) —C$_t$H$_{2t}$OR$^{14}$
   wherein C$_t$H$_{2t}$ has the same meaning as defined above, R$^{14}$ is a straight-chain alkyl having 1 to 6 carbon atoms, a branched alkyl having 3 to 6 carbon atoms, phenyl, a phenyl substituted with at least one chlorine, bromine, fluorine, iodine, trifluoromethyl, an alkyl having 1 to 4 carbon atoms, nitro, cyano, methoxy, phenyl or phenoxy, cyclopentyl, cyclohexyl, or a cyclopentyl or cyclohexyl each substituted with one to four straight-chain alkyl groups having 1 to 4 carbon atoms, or 4) —Z—R$^3$
   wherein Z and R$^3$ have the same meanings as defined above, or 5) —C$_t$H$_{2t}$—CH=C(R$^{15}$)R$^{16}$
   wherein C$_t$H$_{2t}$ has the same meaning as defined above, R$^{15}$ and R$^{16}$ respectively represent a hydrogen, methyl, ethyl, propyl, or butyl, or 6) —C$_u$H$_{2u}$—C≡C—R$^{17}$
   wherein u is an integer from 1 to 7, C$_u$H$_{2u}$ represents a straight-chain or branched alkylene, R$^{17}$ is a straight-chain alkyl having 1 to 6 carbon atoms, E is a hydrogen, or —OR$^{18}$
   wherein R$^{18}$ is an acyl having 1 to 12 carbon atoms, an aroyl having 7 to 15 carbon atoms or R$^2$ (wherein R$^2$ has the same meaning as defined above), and this general formula represents a d-form, l-form or dl-form]

In the aforementioned formula, examples of the pharmacologically acceptable salts include sodium salts, potassium salts and other alkali metal salts, calcium salts, magnesium salts and other alkaline earth metal salts, methylamine salts, dimethylamine salts, trimethylamine salts, methyl piperidine salts, ethanolamine salts, diethanolamine salts, triethanolamine salts, lysine salts and other amine salts, ammonium salts, or basic amino acid salts and the like.

The present prostaglandin I$_2$ derivative can be prepared by, for example, the process described in Japanese Examined Patent Publication No. 6-62599.

Of the present prostaglandin I$_2$ derivatives, the present inventors also found effective derivatives as antihypertensive drugs, ischemic encephalopathy drugs, therapeutic drugs for myocardial infarction, therapeutic drugs for angina pectoris, therapeutic drugs for TIA (transient cerebral ischemic attack), therapeutic drugs for peripheral circulation disorder, antiarteriosclerotic drugs, antithrombotic drugs, antiulcer drugs and intraocular pressure depressants (Japanese Examined Patent Publication No. 6-62599 or Japanese Patent Application No. 7-295789).

These publications, however, fail to indicate that these derivatives have an enhancing effect upon platelet function. Thus, it has not yet been known that these present prostaglandin I$_2$ derivatives have platelet function increment activities, and their usefulness as platelet function increment agents has been first found by the present inventors.

The present prostaglandin $I_2$ derivatives have already been found to have inhibitory activities on platelet aggregation, i.e., to express antithrombic activity by reducing function and hemostatic property of platelets (Japanese Examined Patent Publication No. 6-62599). The present inventors found, however, that the present prostaglandin $I_2$ derivatives enhance the platelet function, that they intensify aggregation of platelets, and that they enhance aggregation and increase hemostatic property of platelets. Thus, the inventors found that the derivatives have opposite activities to known pharmacological activities. The present invention has been accomplished on the basis of the above findings.

The present prostaglandin $I_2$ derivative enhances platelet aggregation induced by other stimulus without, itself, inducing platelet aggregation. As the other stimuli, there may be mentioned ADP, arachidonic acid, collagen, $TXA_2$, serotonin, epinephrine, shearing stress and the like or mixtures of these stimuli. Further, the present prostaglandin $I_2$ derivative is characterized by physiologically antagonizing antiplatelet drugs. These actions can be achieved by reducing cyclic AMP (hereinafter referred to as "cAMP") concentrations in platelets.

The cAMP concentration in platelets is usually maintained at a constant level to thereby preserve platelet function. An increased cAMP concentration inhibits the platelet function and hence expresses an antiplatelet activity. As the present prostaglandin $I_2$ derivative, however, decreases cAMP concentrations in platelets, it enhances the platelet function with antagonizing "the platelet functions, or inhibition of the platelet functions."

As described above, the present prostaglandin $I_2$ derivative is useful for therapy for, among congenital thrombocytopathy, storage pool disease, cyclooxygenase deficiency, $TXA_2$ synthase deficiency, $TXA_2$ receptor abnormality, calcium ionophore refractory and other abnormalities in release, and acquired thrombocytopathy induced by chronic renal failure, liver diseases, blood disorders, extracorporeal circulation or drugs.

Upon administration, the platelet function increment agent of the present invention can be combined with any of excipients, stabilizers and others which are generally used in formulation of pharmaceutical preparations. Examples of such excipients include animal oils, vegetable oils, paraffin, gum arabic, or starches, lactose, sucrose, glucose, dextrin, mannitol and other saccharides, calcium carbonate, calcium sulfate and other salts of inorganic acids, sodium citrate, sodium lactate, magnesium stearate and other salts of organic acids, methyl cellulose, gelatin, poly(ethylene glycol), poly(vinyl alcohol), poly(vinyl pyrrolidone), hydroxyethyl cellulose and other water-soluble polymers, ethanol, glycerin, propylene glycol, sorbitol and other alcohols, sorbitan fatty acid esters, polyoxyethylene sorbitan fatty acid esters, polyoxyethylene fatty acid esters, glycerin fatty acid esters and other surfactants.

The platelet function increment agent of the present invention can be used in a variety of dosage forms, practically including ointments, creams, gels and other semi-solids. It can also be employed as an intravenous injection. In addition, of the derivatives of the present invention, the meta-phenylene-form prostaglandin $I_2$ derivatives can be administered orally, and hence they can be formulated into tablets, powders, granules, pills, capsules and other dosage forms.

The dose of the platelet function increment agent according to the present invention may be 0.02 to 10 mg, preferably, 0.1 to 5 mg per adult once or in some installments, while depending on the symptom, age, status of platelet function decrease of a patient with thrombocytopathy to be administered, dosage form or the like. According to such a therapy, thrombocytopathy can be treated.

EXAMPLES

The present invention will be further described in detail with reference to the following examples, but they should by no means limit the scope of the invention.

Example 1

Action on Platelet Aggregation (1)

A blood specimen sampled from a healthy subject was centrifuged to thereby separate platelet rich plasma (PRP) and platelet poor plasma (PPP). The agent SQ-29548 (refer to Prostaglandins, 1985;29;785), a $TXA_2$ antagonist, was added to PRP, and 1 minute later, a test drug having the following structure (hereinafter referred to as "Compound 1") was added thereto. The experiment was conducted on one group comprising three samples. The test results are set forth in Table 1.

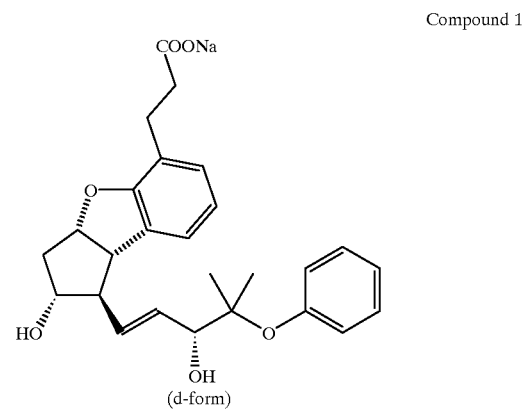

Compound 1
(d-form)

As is apparent from the results, Compound 1 did not induce platelet aggregation in the presence of SQ-29548.

TABLE 1

| Compound 1 ($\mu$M) | Number of Aggregation Induction |
| --- | --- |
| 0.1 | 0 |
| 1 | 0 |
| 10 | 0 |

Example 2

Action on Platelet Aggregation (2)

A blood specimen sampled from a healthy subject was centrifuged to thereby separate platelet rich plasma (PRP) and platelet poor plasma (PPP). SQ-29548, a $TXA_2$ antagonist, was added to PRP, and 1 minute later, platelet aggregation was induced by ADP, and immediately after induction, Compound 1 was added thereto. The experiment was carried out on one group comprising three samples. The test results are shown in Table 2 (*: P<0.05, Paired t-test).

As is obvious from the results, Compound 1 enhanced aggregation of platelets.

TABLE 2

| Compound 1 ($\mu M$) | Platelet Aggregation Rate (%) |
|---|---|
| 0 | 52.0 ± 2.5 |
| 0.1 | 61.3 ± 2.9* |
| 1 | 70.0 ± 3.0 |

Example 3

Antagonistic Action on Inhibition of Platelet Aggregation

A blood specimen sampled from a healthy subject was centrifuged to thereby separate platelet rich plasma (PRP) and platelet poor plasma (PPP). To the PRP was added SQ-29548, a $TXA_2$ antagonist, and then Compound 1 was added one minute after, beraprost sodium (BPS), a prostacyclin derivative, or prostaglandin $D_2$ ($PGD_2$) was added to the PRP, and 1 minute thereafter, aggregation was induced by ADP. The 50% inhibitory concentration ($IC_{50}$) of BPS or $PGD_2$ was then calculated from the results. The experiment was performed on one group composed of three specimens. The results are set forth in Tables 3 and 4 (*: P<0.05, Paired t-test).

As is apparent from these results, Compound 1 physiologically antagonized inhibitory actions of BPS and $PGD_2$ on platelet aggregation.

TABLE 3

| Compound 1 ($\mu M$) | $IC_{50}$ of BPS (nM) |
|---|---|
| 0 | 7.99 ± 1.4 |
| 0.1 | 21.1 ± 4.7 |
| 1 | 36.7 ± 7.4* |

TABLE 4

| Compound 1 ($\mu M$) | $IC_{50}$ of $PGD_2$ (nM) |
|---|---|
| 0 | 38.8 ± 2.5 |
| 0.1 | 71.2 ± 8.2 |
| 1 | 194 ± 28* |

Example 4

A blood specimen taken from a healthy subject was centrifuged to thereby separate platelet rich plasma (PRP). To PRP was added SQ-29548, a $TXA_2$ antagonist, and then Compound 1 was added thereto. After 1 minute, BPS (100 nM) was added to PRP, and then the reaction was stopped by 5% TCA. Thereafter, cAMP in the platelets was extracted and the cAMP concentration was determined with an EIA kit (BIOTRAK cAMP EIA SYSTEM, Amersham). The experiment was carried out on one group composed of five cases. The results are shown in Table 5 (*: P<0.05, Paired t-test).

Compound 1 inhibited cAMP production of BPS in platelets, as is obvious from the test results.

TABLE 5

| Compound 1 ($\mu M$) | cyclic AMP (× basal level) |
|---|---|
| 0 | 8.46 ± 1.8 |
| 0.1 | 6.45 ± 1.4* |
| 1 | 3.98 ± 0.9* |

Example 5

Action on Platelet Aggregation (3)

A blood specimen taken from a healthy subject was centrifuged to thereby separate platelet rich plasma (PRP) and platelet poor plasma (PPP). To PRP was added SQ-29548, a $TXA_2$ antagonist, and 1 minute after, platelet aggregation was induced by ADP, and immediately after induction, any of Compounds 2 to 4 having the following structural formulae was added to PRP. The experiment was performed on one group comprising three subjects. The results are set forth in Table 6 (*: P<0.05, Paired t-test). As is obvious from these results, Compounds 2 to 4 enhanced aggregation of platelets.

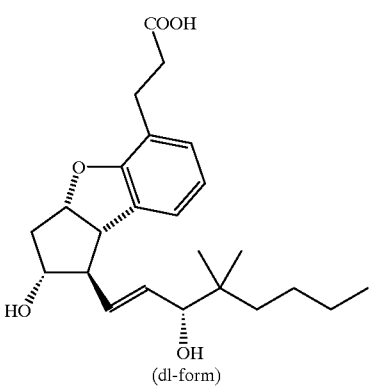

Compound 2
(dl-form)

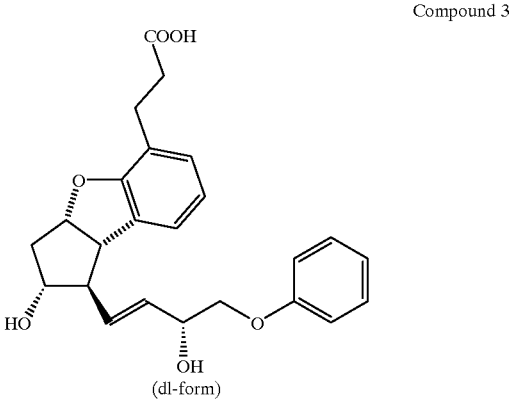

Compound 3
(dl-form)

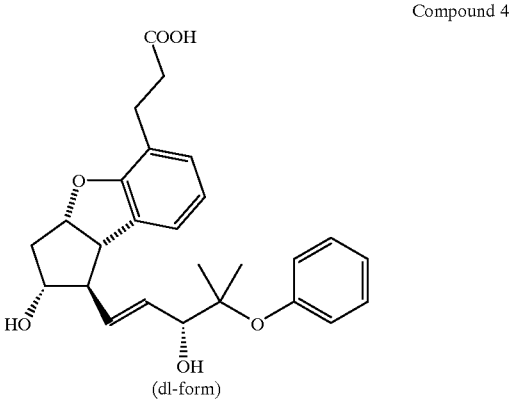

Compound 4
(dl-form)

TABLE 6

| Compound | Platelet Aggregation Rate (%) |
| --- | --- |
| Control | 38 ± 4.9 |
| Compound 2 | 45 ± 6.1* |
| Compound 3 | 43 ± 5.3* |
| Compound 4 | 54 ± 4.1* |

Compound 2 to 4 were respectively used at a concentration within the range of 0.1 to 10 μM.

Medical Applicability

The platelet function increment agent of the present invention does not, by itself, induce platelet aggregation, but has superior activating action on platelets and therefore is greatly useful as a platelet function increment agent.

What is claimed is:

1. A method of antagonizing inhibitory actions upon platelet aggregation, comprising administering to a patient having thrombocytopathy a prostaglandin $I_2$ derivative selected from the group consisting of carbacyclin, isocarbacyclin and a meta-phenylene-form prostaglandin $I_2$ derivative.

2. The platelet function increment method according to claim 1, wherein said meta-phenylene-form prostaglandin $I_2$ derivative is a compound having the following formula (I)

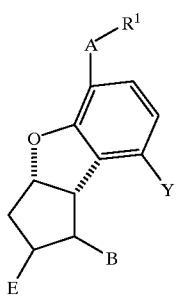

(I)

wherein $R^1$ is, (A) COOR$^2$
  wherein $R^2$ is
  (1) a hydrogen or a pharmacologically acceptable cation,
  (2) a straight-chain alkyl having 1 to 12 carbon atoms or a branched alkyl having 3 to 14 carbon atoms,
  (3) —Z—R$^3$
    wherein Z is a balance bond, or a straight-chain or branched alkylene shown by $C_tH_{2t}$, t represents an integer from 1 to 6, $R^3$ is a cycloalkyl having 3 to 12 carbon atoms or a substituted cycloalkyl having 3 to 12 carbon atoms which is substituted with 1 to 3 substituents $R^4$, wherein $R^4$ is a hydrogen atom or an alkyl group having 1 to 5 carbon atoms,
  (4) —(CH$_2$CH$_2$O)$_n$CH$_3$
    wherein n is an integer from 1 to 5,
  (5) —Z—Ar$^1$
    wherein Z has the same meaning as defined above, Ar$^1$ is phenyl, α-naphthyl, β-naphthyl, 2-pyridyl, 3-pyridyl, 4-pyridyl, α-furyl, β-furyl, α-thienyl, β-thienyl or a substituted phenyl, wherein the substituent is at least one chlorine, bromine, fluorine, iodine, trifluoromethyl, an alkyl having 1 to 4 carbon atoms, nitro, cyano, methoxy, phenyl, phenoxy, p-acetamidebezamide, —CH═N—NH—C(═O)—NH$_2$, —NH—C(═O)—Ph, —NH—C(═O)—CH$_3$ or —NH—C(═O)—NH$_2$),
  (6) —C$_t$H$_{2t}$COOR$^4$
    wherein C$_t$H$_{2t}$ and R$^4$ have the same meanings as defined above,
  (7) —C$_t$H$_{2t}$N(R$^4$)$_2$
    wherein C$_t$H$_{2t}$ and R$^4$ have the same meanings as defined above,
  (8) —CH(R$^5$)—C(═O)—R$^6$
    wherein R$^5$ is a hydrogen or benzoyl, R$^6$ is phenyl, p-bromophenyl, p-chlorophenyl, p-biphenyl, p-nitrophenyl, p-benzamidephenyl or 2-naphthyl,
  (9) C$_p$H$_{2p}$—W—R$^7$
    wherein W is —CH═CH—, —CH═CR$^7$— or —C≡C—, R$^7$ is a hydrogen, or a straight-chain or branched alkyl or aralkyl each having 1 to 30 carbon atoms, p is an integer from 1 to 5, or,
  (10) —CH(CH$_2$OR$^8$)$_2$
    wherein R$^8$ is an alkyl or acyl each having 1 to 30 carbon atoms,
(B) —CH$_2$OH
(C) —C(═O)N(R$^9$)$_2$
  wherein R$^9$ is a hydrogen, a straight-chain alkyl having 1 to 12 carbon atoms, a branched alkyl having 3 to 12 carbon atoms, a cycloalkyl having 3 to 12 carbon atoms, a cycloalkylalkylene having 4 to 13 carbon atoms, phenyl, a substituted phenyl, wherein the substituent has the same meaning as defined in the above item (A) (5), an aralkyl having 7 to 12 carbon atoms or —SO$_2$R$^{10}$, where R$^{10}$ is an alkyl having 1 to 10 carbon atoms, a cycloalkyl having 3 to 12 carbon atoms, phenyl, a substituted phenyl, wherein the substituent has the same meaning as defined in the above item (A)(5) or an aralkyl having 7 to 12 carbon atoms, and two of said substituents R$^9$ may be the same or different provided that when one is —SO$_2$R$^{10}$, the other is not SO$_2$R$^{10}$, or,
(D) —CH$_2$OTHP, where THP is a tetrahydropyranyl group;

A is,
(1) —(CH2)$_m$—
(2) —CH═CH—CH$_2$—
(3) —CH$_2$—CH═CH—
(4) —CH$_2$—O—CH$_2$—
(5) —CH═CH—
(6) —O—CH$_2$— or
(7) —C≡C—
  wherein m is an integer of 1 or 2, Y is a hydrogen, an alkyl having 1 to 4 carbon atoms, chlorine, bromine, fluorine, formyl, methoxy or nitro;

B is

—X—C(R$^{11}$)(R$^{12}$)OR$^{13}$ wherein R$^{11}$ is a hydrogen or an alkyl having 1 to 4 carbon atoms, R$^{13}$ is a hydrogen, an acyl having 1 to 14 carbon atoms, an aroyl having 6 to 15 carbon atoms, tetrahydropyranyl, tetrahydrofuranyl, 1-ethoxyethyl or t-butyl;

X is,
(1) —CH$_2$—CH$_2$—
(2) —CH═CH—
(3) —C≡C—,

R$^{12}$ is
(1) a straight-chain alkyl having 1 to 12 carbon atoms, a branched alkyl having 3 to 14 carbon atoms or, (2) —Z—Ar² wherein Z has the same meaning as defined above, Ar² is phenyl, α-naphthyl, β-naphthyl, or a phenyl substituted with at least one chlorine, bromine, fluorine, iodine, trifluoromethyl, an alkyl having 1 to 4 carbon atoms, nitro, cyano, methoxy, phenyl or phenoxy, or (3) —$C_tH_{2t}$OR¹⁴ wherein $C_tH_{2t}$ has the same meaning as defined above, R¹⁴ is a straight-chain alkyl having 1 to 6 carbon atoms, a branched alkyl having 3 to 6 carbon atoms, phenyl, a phenyl substituted with at least one chlorine, bromine, fluorine, iodine, trifluoromethyl, an alkyl having 1 to 4 carbon atoms, nitro, cyano, methoxy, phenyl or phenoxy, cyclopentyl, cyclohexyl, or a cyclopentyl or cyclohexyl each substituted with one to four straight-chain alkyl groups having 1 to 4 carbon atoms, or (4) —Z—R³ wherein Z and R³ have the same meanings as defined above, or (5) —$C_tH_{2t}$—CH=C(R¹⁵)R¹⁶ wherein —$C_tH_{2t}$ has the same meaning as defined above, R¹⁵ and R¹⁶ respectively represent a hydrogen, methyl, ethyl, propyl, or butyl, or (6) —$C_uH_{2u}$—C≡C—R¹⁷ wherein u is an integer from 1 to 7, $C_uH_{2u}$ represents a straight-chain or branched alkylene, R¹⁷ is a straight-chain alkyl having 1 to 6 carbon atoms, E is a hydrogen, or —OR¹⁸ wherein R¹⁸ is an acyl having 1 to 12 carbon atoms, an aroyl having 7 to 15 carbon atoms or R², wherein R² has the same meaning as defined above, and this general formula represents a d-form, an l-form or a dl-form.

3. The platelet function increment method according to claim 1, wherein said increment agent enhances platelet aggregation induced by other stimulus without, by itself, inducing platelet aggregation.

4. The platelet function increment method according to claim 1, wherein said increment agent physiologically antagonizes an antiplatelet drug.

5. The platelet function increment method according to claim 1, wherein said increment agent inhibits increase of cyclic AMP concentrations in platelets.

6. The platelet function increment method according to claim 1, which is used for the purpose of treating an abnormality in release among congenital thrombocytopathy, or an acquired thrombocytopathy.

7. The platelet function increment method according to claim 6, wherein said abnormality in release is storage pool disease, cyclooxygenase deficiency, thromboxane $A_2$ synthase deficiency, thromboxane $A_2$ receptor abnormality or calcium ionophore refractory.

8. The platelet function increment method according to claim 6, wherein said acquired thrombocytopathy is induced by chronic renal failure, a liver disease, a blood disorder, extracorporeal circulation or a drug.

* * * * *